United States Patent [19]

Pawlak et al.

[11] Patent Number: 5,135,538
[45] Date of Patent: Aug. 4, 1992

[54] ELECTROMAGNETICALLY CONTROLLED HEART VALVE

[75] Inventors: Andrzej M. Pawlak, Troy, Mich.; David B. Young, Jackson, Miss.

[73] Assignees: General Motors Corporation, Detroit, Mich.; University of Mississippi Medical Center, Jackson, Miss.

[21] Appl. No.: 709,782

[22] Filed: Jun. 3, 1991

Related U.S. Application Data

[63] Continuation of Ser. No. 412,708, Sep. 29, 1989, abandoned.

[51] Int. Cl.⁵ .................. A61F 2/24; F16K 15/00; F16K 17/00; F16K 21/04
[52] U.S. Cl. ........................ 623/2; 137/527; 137/512
[58] Field of Search ............ 623/2; 137/512, 527; 251/65, 298

[56] References Cited

U.S. PATENT DOCUMENTS

| | | | |
|---|---|---|---|
| 3,974,854 | 8/1976 | Kurpanek | 137/512 |
| 4,532,659 | 8/1985 | Kaster | 623/2 |
| 4,605,408 | 8/1986 | Carpentier | 623/2 |
| 4,979,955 | 12/1990 | Smith | 623/2 |

Primary Examiner—David Isabella
Assistant Examiner—Elizabeth M. Burke
Attorney, Agent, or Firm—C. R. Meland

[57] ABSTRACT

A unidirectional flow heart valve includes a passageway having an inlet side and an outlet side. A disk occluder is disposed within the passageway. The disk occluder has a closed position wherein the disk occluder occludes fluid flow through the passageway and an open position wherein the disk occluder permits fluid flow through the passageway. A fulcrum causes the disk occluder to pivot off center between the open and closed positions. An electromagnetic control mechanism forces the disk occluder to remain closed when energized until a predetermined net pressure is reached against the disk occluder. When the electromagnetic control mechanism is either selectively deenergized or the force on the occluder disk is greater than the holding force of the electromagnetic control mechanism, the disk occluder is released from the closed position to pivot on the fulcrum in response to fluid pressure.

8 Claims, 5 Drawing Sheets

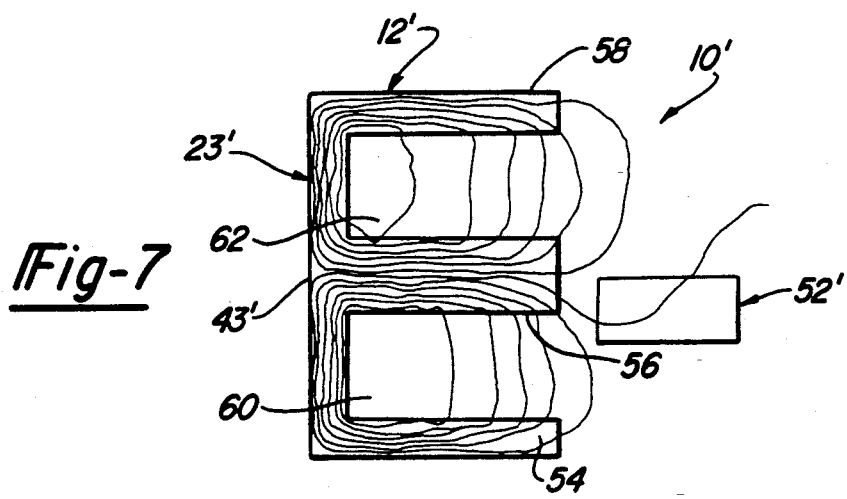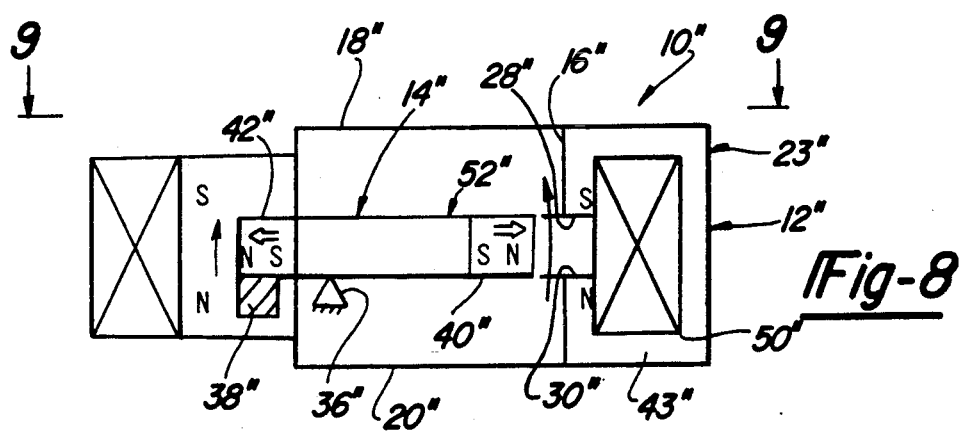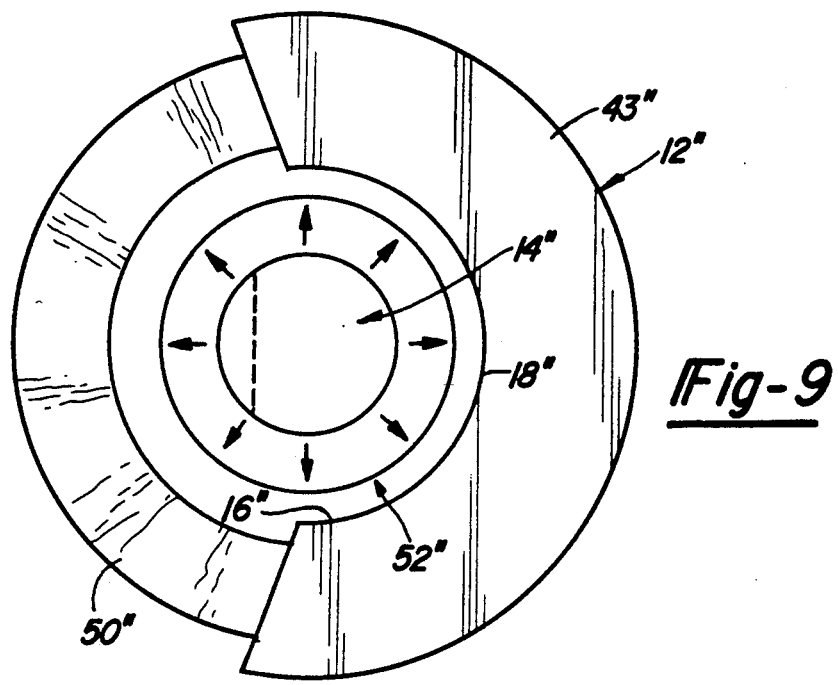

ELECTROMAGNETICALLY CONTROLLED HEART VALVE

"This invention was made with government support under National Institutes of Health Grant Number 5 R01 HL21435-10. The government has certain rights in the invention." "This is a continuation of application Ser. No. 07/412,708 filed on Sep. 26, 1989, abandoned.

TECHNICAL FIELD

This invention relates generally to unidirectional fluid flow prosthetic heart valves.

BACKGROUND ART

In a normal heart, four heart valves control the passage of blood between the chambers in the heart. These valves control unidirectional fluid flow of the blood. State of the art medical techniques have enabled specialists to replace defective heart valves with prosthetic heart valves.

An example of a state of the art prosthetic heart valve is disclosed in the U.S. Pat. No. 4,532,659 to Kaster, issued Aug. 6, 1985. The valve includes a free floating rotatable, pivotable disk occluder mounted for pivoting movement on a proximally positioned control unit. The control unit defines an off center fulcrum upon which the disk occluder pivots between an open and a closed position. In operation, when blood pressure on the proximal side of the disk occluder increases and exceeds the blood pressure on the distal side of the disk occluder, the disk occluder moves from an occluded or closed position to the open position. This transition between open and closed positions is actuated purely by the asymmetric blood pressures on the inlet and outset sides of the disk occluder. There is no additional means for controlling either the opening or closing of the valve.

The U.S. Pat. No. 3,974,854 to Kurpanek, issued Aug. 17, 1976 discloses a permanently implantable artificial heart including a unidirectional fluid flow valve. Each valve includes two valve flaps which open in response to an increased blood pressure gradient on the inlet side of the flaps and close due to magnetic attraction when the blood pressure gradient reverses. The valve flaps contain a permanent magnet which is magnetically attracted to a permanent magnet mounted rigidly in the outer wall of the support structure. This device includes means for actuating the closing of the valve flaps but includes no means for controlling the opening of the valve flaps independent of the blood pressure gradient on the two sides of the valve flaps.

The U.S. Pat. No. 4,605,408 to Carpentier, issued Aug. 12, 1986, discloses a cardiac valve having a device which insures controlled opening of the valve when blood pressure is balanced on both sides of the mobile element or disk occluder of the valve. The mobile element of the valve is either mechanically moved to an open position by a spring when the pressure on the mobile element is equal on both sides or the valve includes magnets disposed opposite each other, the poles of the same sign facing each other. One of the magnets is within the ring about the mobile element and the other magnet is embedded within the mobile element. The two magnets repulse each other thereby opening the valve slightly when the pressures on each side of the valve are equal.

. It is desirable, experimentally and clinically, to be able to control when a prosthetic heart valve opens. Experimentally, it is beneficial for researchers to be able to manipulate the flow of blood through the heart under controlled experimental conditions. Clinically, the control of the opening of the valves, as well as the control of the closing of the valves, provides the clinician with new tools for therapeutic application.

SUMMARY OF THE INVENTION

In accordance with the present invention there is provided a unidirectional fluid flow heart valve including control means for selectively releasing the valve from a closed position.

More specifically, a unidirectional fluid flow valve is provided which includes a passageway having an inlet side and an outlet side, a disk occluder disposed within the passageway having a closed position wherein the disk occludes fluid flow through the passageway and an open position wherein the disk occluder permits fluid flow through the passageway, and fulcrum means for causing the disk occluder to pivot off center between the open and closed positions. Control means selectively releases the disk occluder from the closed position to pivot in response to fluid pressure.

FIGURES IN THE DRAWINGS

Other advantages of the present invention will be readily appreciated as the same becomes completely understood by reference to the following detailed description when considered in connection with the accompanying drawings wherein: FIG. 1 is a perspective view of the outlet side of a unidirectional fluid flow valve constructed in accordance with the present invention;

FIG. 7 is a static finite element analysis of the magnetic field of the second embodiment when the electromagnet thereof is energized and the disk occluder is in the closed position;

FIG. 8 is a schematic cross sectional view of a third embodiment of the present invention;

FIG. 9 is a plan view taken substantially along lines 9—9 of FIG. 8;

DETAILED DESCRIPTION OF THE INVENTION

Figure 1:
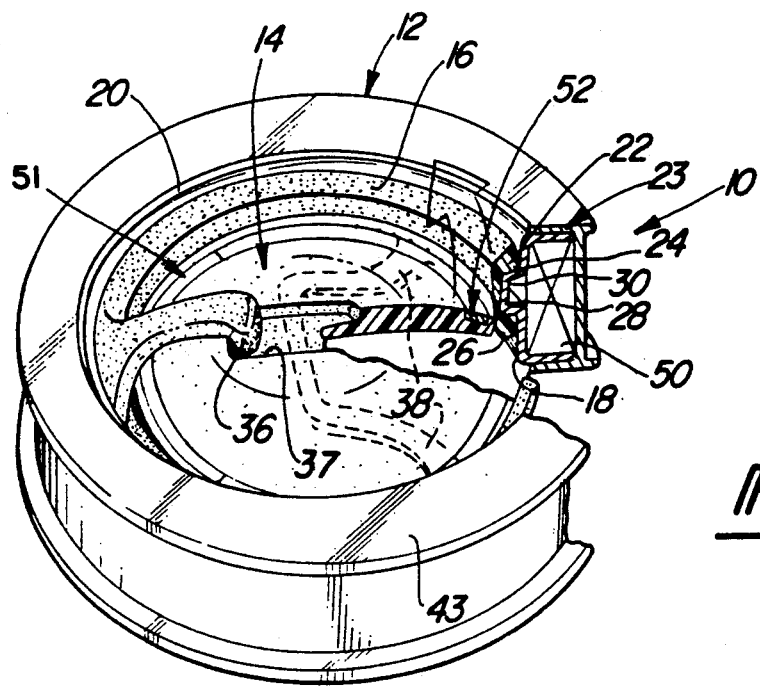
Figure 2:
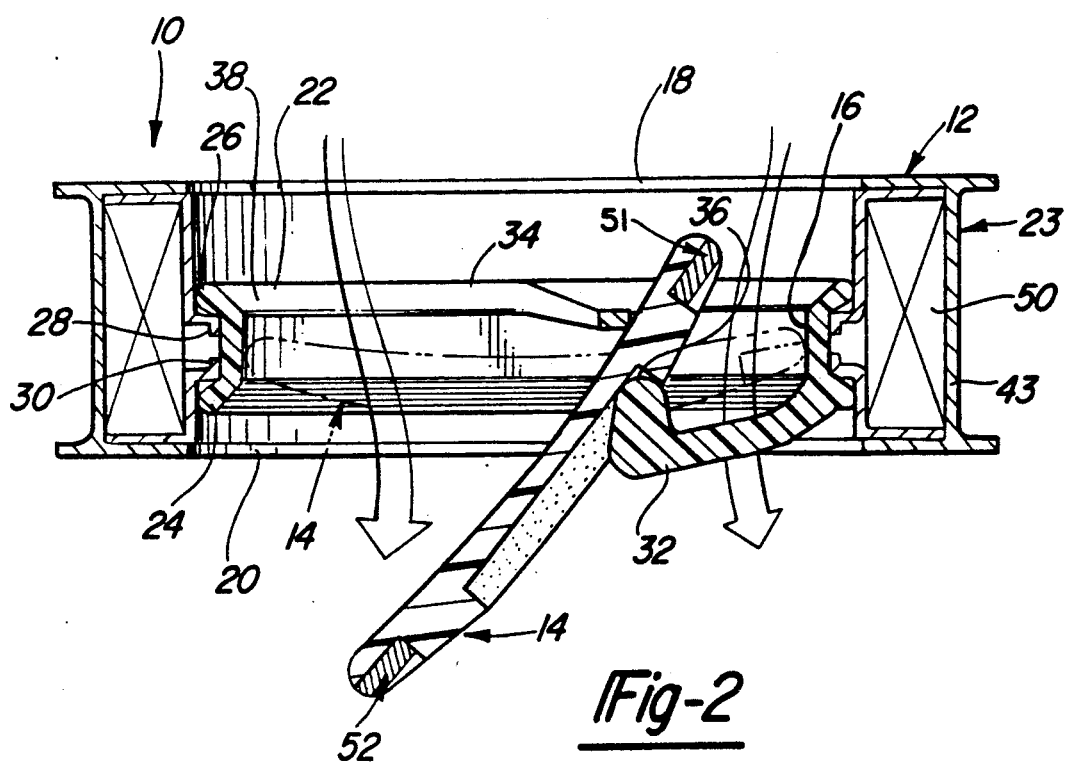
FIG. 2 is a cross sectional view of the valve shown in the open position in solid lines and in the closed position in interrupted lines.

A unidirectional fluid flow heart valve constructed in accordance with the present invention is generally shown at 10 in FIGS. 1-4. The valve 10 includes a valve housing generally indicated at 12 and a disk occluder 10 generally indicated at 14. The housing 12 has a passageway 16 extending therethrough. The passageway 16 has an inlet side 18 and an outlet side 20.

The housing 12 includes a supporting ring 22 and an electromagnet generally indicated at 23. The support ring 22 is mounted within the passageway 16. The ring 22 includes outwardly projecting arms 24,26 which are secured over outwardly projecting poles 28,30 of the electromagnet 23. A projecting finger 32 and U-shaped control member 34 extend from the ring 22 into the passageway 16. The disk 14 is supported to pivot between an open position shown in solid lines in FIG. 2 and the closed position shown in interrupted lines in FIG. 2 between a projecting finger 32 and the U-shaped control member 34. The finger 32 includes an end portion 36 defining a fulcrum for causing the disk occluder 14 to pivot off center between the open and closed positions. The end portion 36 engages a depression 37 in the disk occlunder 14 to prevent rotation of the disk occluder in its own plane. The control member 34 includes shoulders 38. The shoulders 38 function as stops or abutments engaged by the disk occluder 14 in the closed position.

Figure 3:
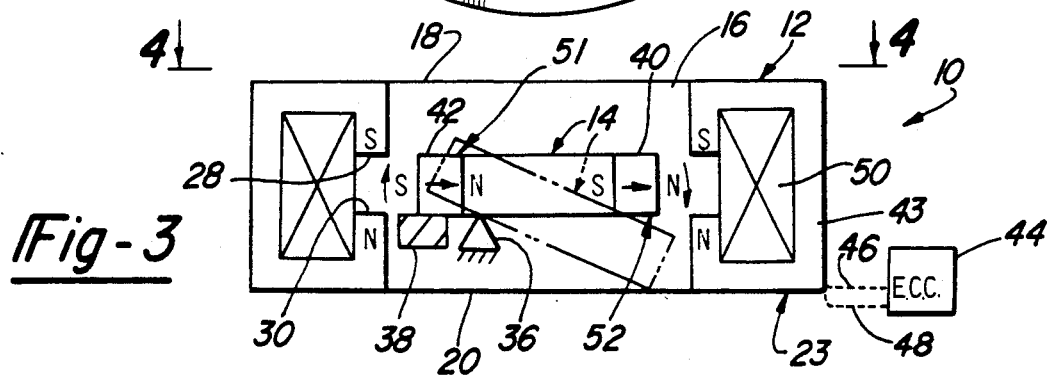
FIG. 3 is a schematic cross sectional view of the valve.

In the closed position, fluid flow through the passageway 16 is occluded and in the open position fluid flow through the passage 16 is permitted. The fulcrum 36 divides the disk occluder 14 into a larger area portion 40 on one side of the pivot axis defined by the fulcrum 36 and a smaller area portion 42 on the opposite side of the pivot axis defined by the fulcrum 36. The stop 38 engages the outlet side surface of the smaller area portion 42 when the disk occluder 14 is in closed position as shown in FIG. 3 in solid lines.

The electromagnet 23 comprises a coil 50 and a magnetic circuit 43. The coil is enclosed within the magnetic circuit 43 which is of toroidal configuration with a C-shaped cross section, in the manner of a C-core. The magnetic circuit 43 is constructed of a ferromagnetic material and includes an air gap between a pair of spaced magnetic, poles 28,30. Each of the poles extends circumferentially of the disk occluder 14 in close proximity with the periphery thereof. The energization of the electromagnet 23 is controlled by an electronic control circuit 44. For this purpose, the terminals of the coil 50 are connected through conductors 46,48 to the control circuit 44, as shown schematically in FIG. 3. As will be described subsequently, the control circuit 44 is adapted to energize the electromagnet 23 with a DC current of controllable magnitude and time duration. If desired, the current may be supplied by the control circuit in the form of repetitive pulses of uniform, predetermined amplitude which are triggered in synchronism with the heart beat. The energization of the coil 50 with direct current polarizes the pole 28 as a south pole and pole 30 as a north pole.

Figure 4:
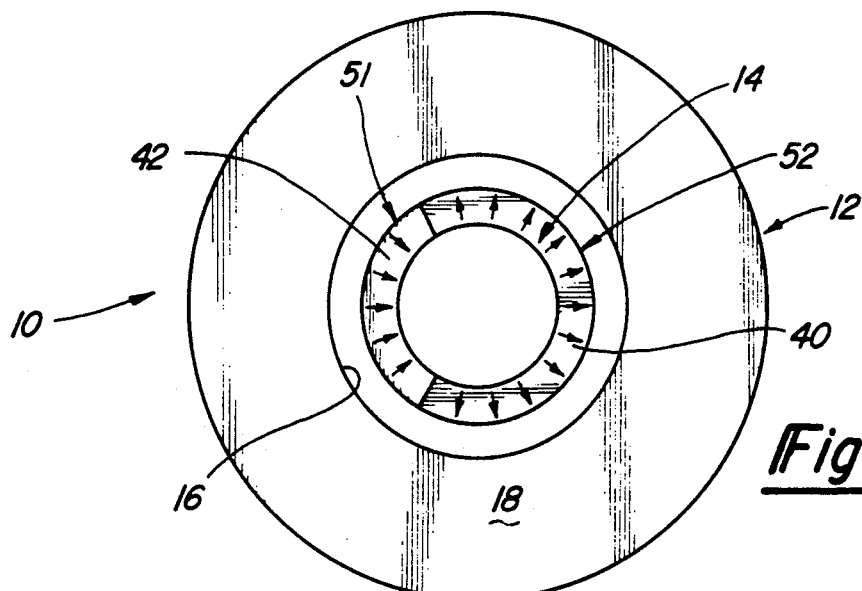
FIG. 4 is a plan view taken substantially along lin3 4—4 of FIG. 3.

A pair of permanent magnets 51 and 52 are embedded within and about the radial distal aspect of the disk occluder 14. As shown in FIG. 4, the permanent magnet 52 is disposed about the larger area portion 40 of the disk occluder 14 and has a radially distal north pole and a radially proximal south pole. On the smaller area portion 42 of the disk occluder 14, the permanent magnet 51 has a radially distal south pole and a radially proximal north pole.

The electromagnet 23 comprising the coil 50 and magnetic circuit 43 in combination with the permanent magnets 51 and 52 provide control means for selectively releasing the disk occluder 14 from the closed position to pivot on the fulcrum 36 in response to fluid pressure, as discussed below. As shown schematically in FIG. 3, the disk valve 14 and is pivotally supported on the fulcrum 36. The outer aspect of the electromagnet 23 would be adapted to be fixedly connected to heart tissue to thereby provide an outside stationary electromagnet 23. The magnetic circuit 43 is energized by a DC current such that the polarity of inlet side pole 28 about the larger portion 40 is opposite to the radially distal polarity of the permanent magnet 51. The distal radial polarity of the permanent magnet 51 about the smaller area portion 42 is the opposite of the outlet side pole 30. Upon energization, the electromagnet coacts with the magnets to exert attractive and repulsive forces to maintain the disk occluder in the closed position until either the net force of the fluid on the inlet side of the disk occluder 14 is greater than the holding force or until deenergization of the electromagnet. In the former instance, the electromagnet would be deenergized after the blood pressure force overcomes the holding force.

Figure 5:
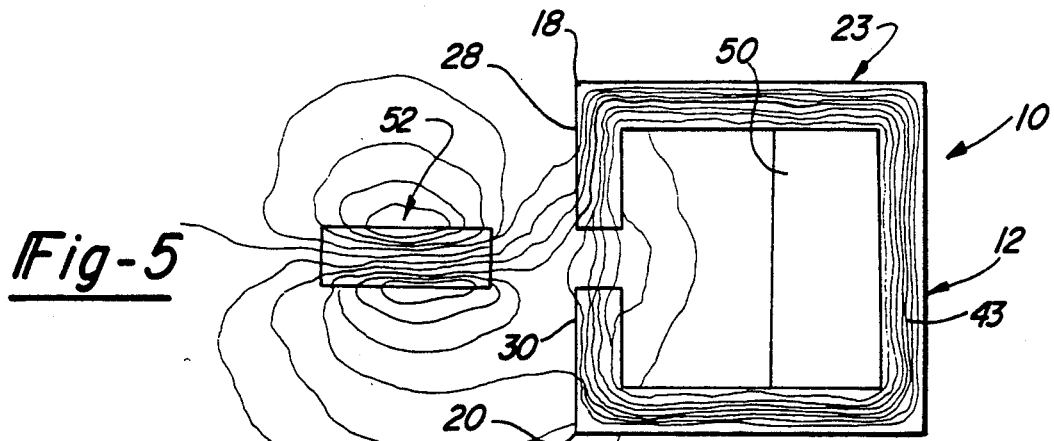
FIG. 5 shows a static finite element analysis of the magnetic field of the valve when the electromagnets thereof are energized and the disk occluder is in the closed position.

As shown by the static finite element analysis in FIG. 5, this configuration develops a force on the disk 14 having a component tending to hold the disk in the closed position. This configuration develops maximum force when the disk occluder is in the horizontal or closed position shown in solid lines in FIG. 3. Thus, the magnetic forces maintain the disk occluder 14 in a stable closed position.

When the coil 50 is energized, the south pole 28 attracts and the north pole 30 repulses north pole of the permanent magnet 52 about the larger area portion 40 of the disk occluder 14 and the north pole 30 attracts and the south pole 28 repulses the south pole of the permanent magnet 51 about the smaller area portion 42 of the disk occluder 14. The stop 38 prevents the disk occluder 14 from pivoting past the point where the electromagnet 23 creates its maximum attraction forces. In the absence of energization of the electromagnet 23 by current through the coil, the disk occluder 14 will move from its closed position to the open position in response to a predetermined threshold value of differential pressure across the disk occluder. When electromagnet 23 is energized, it provides a holding force in accordance with the magnitude of the DC current in the coil and prevents the disk occluder from opening unless the force in the opening direction produced by the differential fluid pressure across the disk occluder exceeds the holding force. The holding force created by the electromagnet 23 is controlled so that it is sufficiently greater than that force created by the differential blood pressure so that the disk occluder 14 is held in the closed position until a predetermined differential pressure is reached. If the coil is deenergized, the magnetic force decays and the blood pressure moves the disk occluder 14 to the open position. Alternatively, if a magnetic force is achieved which is less than the maximum achievable blood pressure, then the force of the blood pressure may overcome the holding force and open the valve 10.

This embodiment of the present invention provides very good sealing so as to prevent blood leakage and blood cell damage. This is achieved by the control of the horizontal or closed position of the disk occluder 14. However, the first embodiment of the present invention requires permanent magnets which are opposite polarity in the radial direction. Such a magnetic configuration requires the disk occluder 14 to be prevented from rotating in its own plane. Rotation of the disk occluder 14 would disrupt the orientation of the radially asymmetric permanent magnets 51 and 52.

Figure 6:
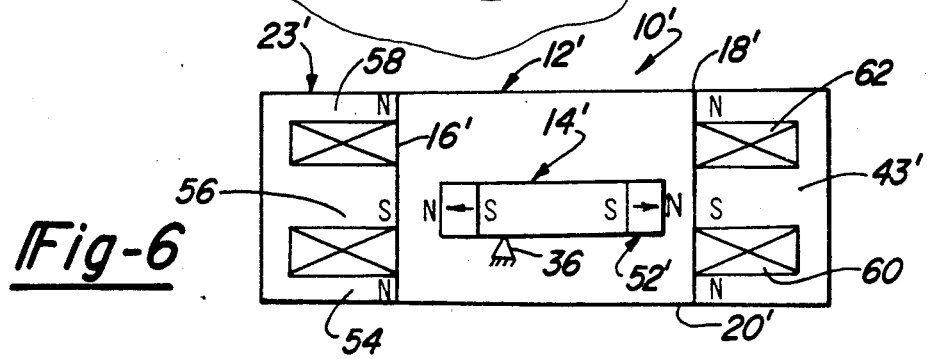
FIG. 6 is a schematic representation of a second embodiment of the invention in cross section.

FIGS. 6 and 7 show a second embodiment of the present invention which includes a rotatable disk occluder. Primed numbers are used to show similar structure between the two embodiments.

The second embodiment generally shown at 10' includes an electromagnet 23' and a permanent magnet 52'. The permanent magnet 52' is disposed about and embedded within the distal aspect of the disk occluder 14', the permanent magnet 52' having symmetric radial polarity. By symmetric radial polarity, it is meant that the permanent magnet has a radially distal north pole completely about its distal periphery and a radially proximate south pole. Of course, depending upon the related polarity of the electromagnet 23', the polarity may be reversed. Accordingly, there is no limitation placed on the disk occluder 14' which would prevent it from being rotatable.

The electromagnet 23 comprises a pair of coils 60,62 and a magnetic circuit 43'. The magnetic circuit 43' is of toroidal configuration with an E-shaped cross section, in the manner of an E-core. The magnetic circuit is constructed of a ferromagnetic material and includes three radially inwardly extending pole pieces terminating in an intermediate pole 56 and a pair of outer poles 54,58. The coil 60 is disposed in the annular space between pole pieces 54,56 and the coil 62 is disposed in the annular space between the pole pieces 58,56. The electromagnet 23' is energized by supplying the coils 60,62 with a DC current flowing in opposite directions in the two coils. This polarizes the intermediate pole piece 56 as a south pole and the pole pieces 54,58 as north poles. Thus, the north pole of the permanent magnet 52' is attracted to the south pole of the intermediate pole piece 56, and repulsed by north pole pieces 54,58 pieces which tend to hold the disk occluder 14' in alignment with the intermediate poles. Energization of the electromagnet 23' holds the disk occluder 14' in the closed or horizontal position, as shown in FIG. 6.

A static finite element analysis of the magnetic field for the second embodiment 10' is shown in FIG. 7. When the permanent magnet 52' is in direct alignment with the pole piece 56, there is no component of magnetic force acting on the disk occluder 14' tending to pivot it about its pivotal axis. In this arrangement, such a component of force is not developed until a slight pivotal movement of the disk occluder 14' occurs. This permits some leakage around the disk occluder 14' when such positioning is utilized as the closed position or horizontal position for the disk occluder. Thus, with the disk occluder 14' in a closed position, it is in an unstable equilibrium.

In order to minimize or prevent leakage of the valve in a closed position, the valve may be designed so that in the closed position, the disk occluder 14' is inclined slightly relative to the plane of the pole piece 56 so that a component of magnetic force is developed which holds the disk occluder 14' in the closed position. In such closed position, the magnetic forces maintain the disk occluder 14' in a stable closed position.

Figure 10:
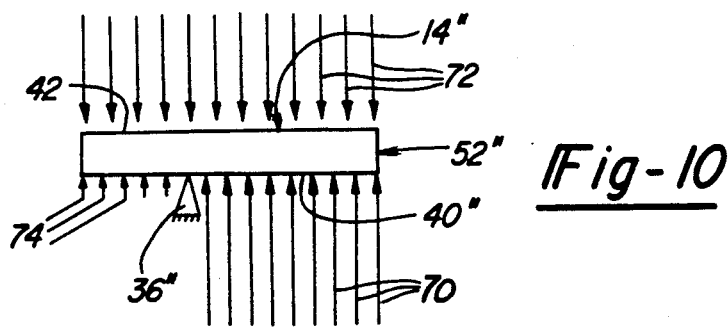
FIG. 10 is a schematic representation illustrating pressure and magnetic forces on the occluder disk of the third embodiment, shown in cross section.

A third embodiment of the invention is shown in FIGS. 8–10. Double primed numbers are used to indicate like structure between the third embodiment and the prior embodiments.

The device 10'' includes a radially symmetric permanent magnet 52'' disposed about the distal aspect of the disk occluder 14''. The electromagnet 23'' introduces asymmetric magnetic force around the permanent magnet 52'' when energized wherein the force is greater on the larger area portion 40'' than the smaller area portion 42'' of the disk occluder 14'' to selectively release the disk occluder 14'' when the electromagnetic 23', is de-energized allowing the disk occluder 14'' to open in response to fluid pressure or when net blood pressure force on the inlet side of the disk occluder 14 is greater than the holding force of the electromagnet 23''.

More specifically, the electromagnet 23'' includes a magnetic circuit 43'' comprising an annular coil 50'' with a flux path around the coil of ferromagnetic material, i.e., a ferromagnetic core on one side of the pivot axis and a flux path of nonmagnetic material, i.e., an air core on the other side. The ferromagnetic core is in the form of a substantially C-shaped toroidal segment. The coil 50'' has a portion within the ferromagnetic core about the larger area portion 40'' of the disk occluder 14'' and a remaining portion with an air core extending about the smaller are portion 42'' of the disk occluder 14''. This configuration introduces magnetic asymmetry around the pivot axis defined by the fulcrum 36''. When the electromagnet 23'' is energized by a DC current in coil 50'', a magnetic holding force is exerted on the disk occluder 14''. The permanent magnet 52'' is attracted to the south pole 28'', and repulsed by the north pole 30'', which applies a closing force to the disk occluder 14'' tending to rotate it in the counterclockwise direction as viewed in FIG. 8. The permanent magnet 52'' is also attracted by the south pole of the air core coil and repulsed by the north pole of air core and this produces an opening force on the disk occluder 14''. Since the closing force is produced by the ferromagnetic core portion of the electromagnet with higher flux density and greater length, it is much greater than the opening force produced by the air core portion of the electromagnetic. The net holding force is the difference between the closing force and the opening force and is opposed by the blood pressure acting on the disk occluder 14''. This force relationship is illustrated in FIG. 10 where arrows 70 illustrate the closing force created by the electromagnet acting on the permanent magnet 52'' about the larger area portion 40'', arrows 72 illustrate the total force of blood pressure on the inlet side of the disk occluder 14'' and arrows 74 represent the opening force created by the electromagnet and the permanent magnet 52'' disposed about the smaller area portion 42'' of the disk occluder 14''. To hold the disk occluder 14'' in a closed position, the difference between the closing force and the opening force exerted by the electromagnet must be greater than the net opening force of the blood pressure on the inlet side.

This geometry of the valve 10'' enables the use of an artificial valve with rotary disk movement to develop holding disk force in a horizontal position. The controllable heart valve 10'' is not as efficient electromagnetically as the first embodiment indicated at 10 because of the negative force developed during operation. However, the third embodiment indicated at 10" can be used for structures including a rotary disk where these disks are flat and thicker which is helpful when the permanent magnet is inserted in a horizontal position. This configuration further requires a smaller off center pivot axis thereby requiring less magnetic holding force be developed. This compensates to a certain degree for the negative force in the design.

The permanent magnets utilized with the present invention are preferably extremely high strength force producing magnets. An example of such a magnet is constructed with the material Neodymium sold under the trade name MQIII by General Motors Corporation, Detroit, Mich. The support ring 22 must be made from a nonmagnetic material. Preferably, titanium is used to construct the support ring. The disk 14, 14', 14" is made from a nonmagnetic material, preferably a carbon composite or plastic material.

Figure 13:
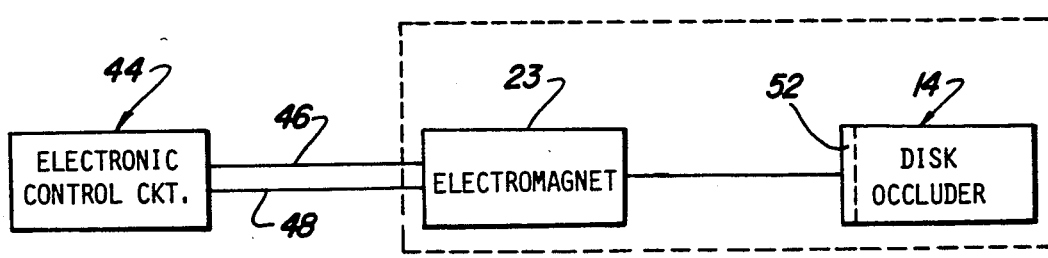
FIG. 13 is a block diagram schematically illustrating the control circuit of the invention.

Each of the embodiments of the present invention provides control means for selectively releasing the disk occluder to pivot on the fulcrum in response to fluid pressure. FIG. 13 schematically represents the control circuit of the invention. An electronic control circuit 44 controls the energization of the electromagnet 23 which exerts a holding force against opening of the disk occluder by magnetic attraction of the permanent magnet 52. The control circuit 44 is a pulse-width modulator which can be operated at a constant frequency and variable duty-cycle, that is the relative consecutively occurring energization and deenergization times of the coil is controlled such that the energization time can be varied.

Figure 11:
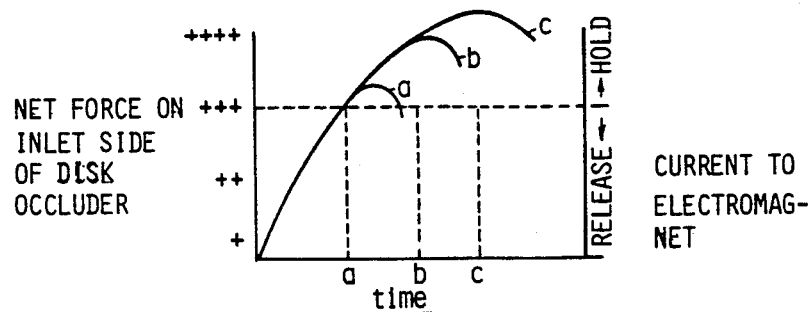
FIG. 11 is a chart schematically plotting net blood pressure force on the inlet side of the disk occluder and current to the electromagnet of sufficient strength to hold the disk occluder closed versus time.
Figure 12:
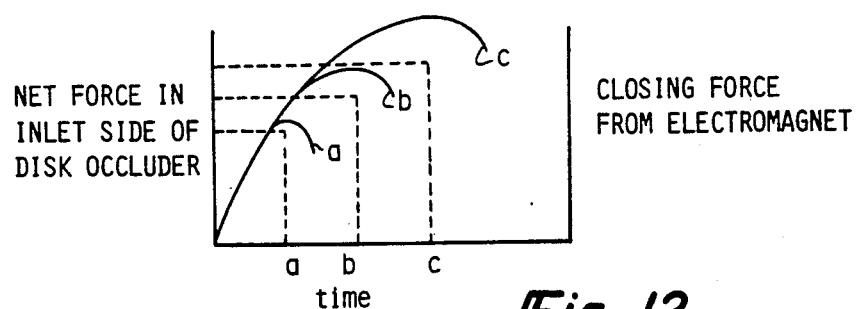
FIG. 12 is a chart schematically plotting net force on the inlet side of the disk occluder and closing force from the electromagnet versus time.

FIGS. 11 and 12 graphically illustrate the operation of the present invention to controllably maintain the heart valve closed. The solid line in FIG. 11 schematically shows the rise in the net blood pressure force on the inlet side of the disk occluder over time. Blood pressure is shown quantitatively by plus signs (+). The interrupted lines show the current to the electromagnet. There is no attempt to show experimental data of the effect of the release function, but rather the chart illustrates the hypothesis that release can occur at various points in time, independent of blood pressure forces if the holding force is greater than any achievable blood pressure prior to failure of the heart. The present invention can be utilized to maintain the heart valve in the closed position by supplying sufficient current to the electromagnet to hold the valve closed independent of blood pressure. Upon a decrease of current at times a, b, or c, decay of the magnetic force allows a release of the disk occluder from the closed position thereby allowing it to open in response to the blood pressure.

Alternatively, as shown in FIG. 12, a specific holding force can be generated by the electromagnet which can be overcome by a physiological rise in blood pressure. Thusly, as the blood pressure exceeds the critical opening force to overcome the holding force, the valve will open and pressure on the disk will decrease. The current to the valve will then be discontinued until pressure across the valve reverses and the valve is closed by back pressure. The cycle is then repeated and valve control is achieved. The chart shows that the holding force can be varied to achieve different biological effects. The chart is schematic and shows hypothetical data and makes no attempt to imitate actual experimental data.

A researcher or clinician can thereby fine-tune the opening and closing of the heart valve to obtain either experimental results or a desired clinical situation in a patent. As the pacemaker controls the heart beat, the present invention provides an additional means for controlling blood flow in response to or independent of blood pressure.

Figure 14:
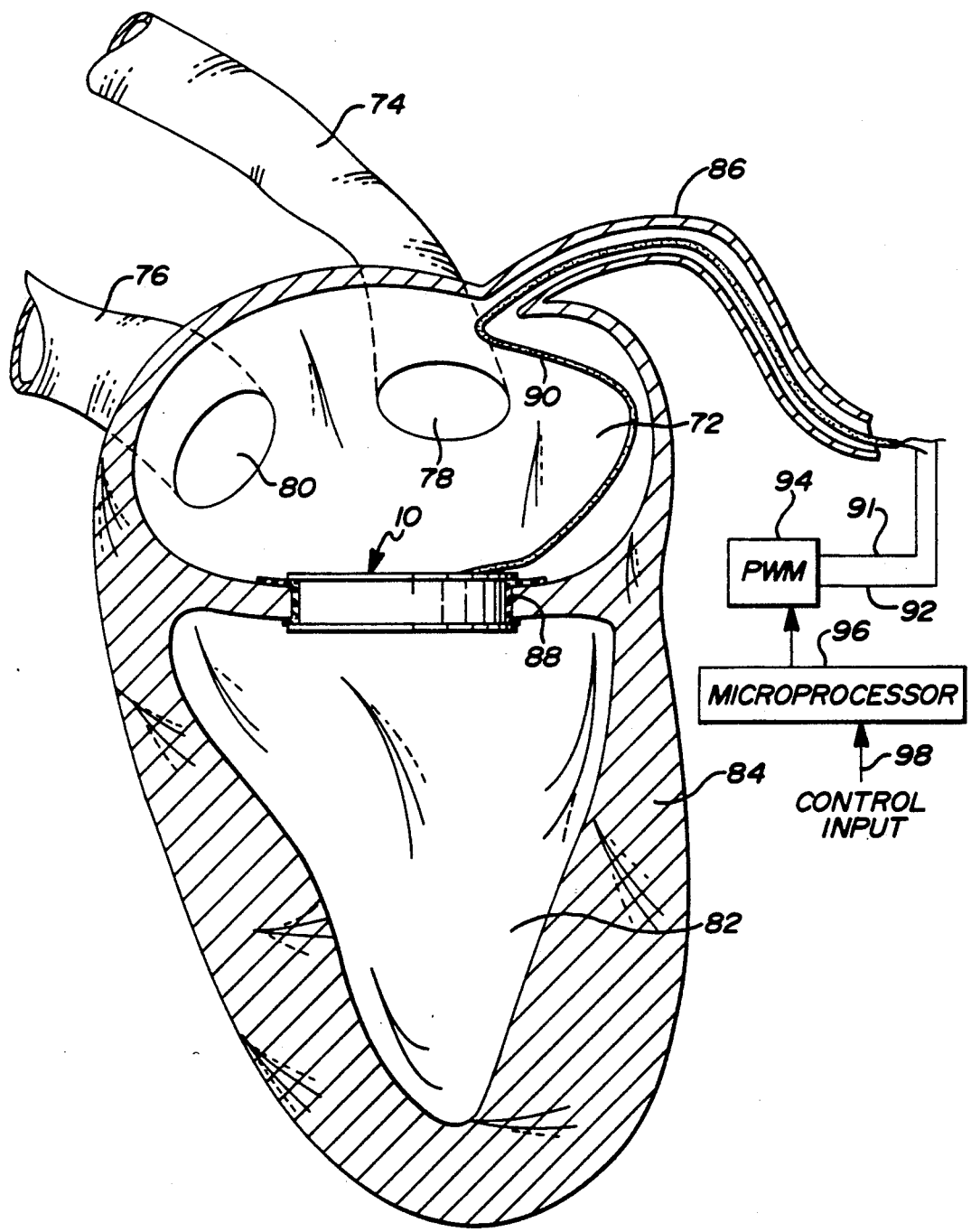
FIG. 14 is a sectional view of a heart illustrating the position of the heart valve and the manner in which the heart valve is controlled.

Referring now to FIG. 14, a cross-section of a heart is illustrated with the heart valve shown implanted. In FIG. 14, the reference numeral 72 designates the cavity of the left atrium. Reference numerals 74 and 76 designate pulmonary veins and 78 and 80 designate entrances of the pulmonary veins. Reference numeral 82 designates the cavity of the left ventricle and 84 designates the wall of the left ventricle. Reference numeral 86 designates a left atrial appendage. It can be seen in FIG. 14 that the heart valve 10 is disposed between the left atrium cavity 72 and the left ventricle cavity 82.

The procedure for implanting the heart valve 10 will now be described in relation to implanting the valve in an animal. The animal is anesthetized, the chest is opened and the blood is diverted from the great veins of the chest through an extracorporal heart-lung machine and back to the aorta. The left atrium is opened to expose the mitral valve. The valve is excised completely and the valve 10 is placed in the opening between the left atrium cavity 72 and the cavity 82 of the left ventricle. A sewing ring 88 made of dacron cloth is attached to the valve and is used to sew the valve to the heart tissue. The power lead wires that are connected to coil 50 are contained in a plastic tubing 90 that may be formed of teflon and which may have an outside diameter of about 0.03 inches. From the valve, the tubing and lead wires pass through the chamber of the left atrium and emerge through a stab in the left atrial appendage 86. A purse-string suture is placed around the stab to secure the opening. From the heart, the lead wires pass dorsally through the chest and through the space between the second and third ribs and then through the skin to emerge between the scapulae. The power leads are protected on the surface of the animal by covering the point of emergence from the skin and their external path with a protective jacket and harness.

In FIG. 14, the valve disk 14 (not illustrated) of valve 10 opens by pivoting toward the left ventricle cavity 82 against the electromagnetic force developed by energization of coil 50. Putting it another way, the inlet of valve 10 faces the left atrium cavity 72 and the valve outlet faces left ventricle cavity 82. Pressure in left atrium cavity 72 develops a force tending to open the valve and this force is opposed by the electromagnetic force developed due to energization of coil 50.

In FIG. 14, the power leads that are connected to coil 50 and which are external of the animal are designated as 91 and 92. These leads are connected to a pulse-width modulator 94 which can be operated at a constant frequency and variable duty-cycle or pulse-width. By way of example and, not by way of limitation, the pulse modulator may have a direct input voltage of 24 volts which is pulse-width modulated. Coil 50 may be 136 turns of No. 36 AWG wire with a coil resistance of about 13.3 ohms. The energization and deenergization times of coil 50, which are controlled by pulse-width modulator 94, are such that the heat generated by coil 50 will not damage heart tissue. In this regard, it is noted that heat generated in the coil is transferred to the blood flowing over the housing and coil of the valve.

The on-time or duty cycle of pulse-width modulator 94 is controlled by a microprocessor 96 which has a control input 98. Assume, for example, that an investigator wishes to control left atrial pressure at a set level for an extended period of time. To accomplish this, a pressure sensor would be implanted in the left atrium cavity 72. The output of the pressure sensor is digitized and provided as an input to microprocessor 96 via control input line 98. The microprocessor is programmed to compare current left atrium pressure with a desired pressure or set-point pressure. If, for example, the current pressure is less than the set-point pressure, the microprocessor provides a signal to pulse-width modulator 94 to increase the duty-cycle or period of time that coil 50 is energized. This increases the current supplied to the coil and as a result, the strength of the electromagnetic field generated by the coil is increased. This increase is field strength will hold the disk of the valve in the closed position until a higher level of atrial pressure is reached before the valve opens. The programmed microprocessor will continue to operate in this manner, increasing the power to the coil until the pressure level in the left atrium rises up to the set-point. If the left atrial pressure rises above the set-point, the microprocessor will operate in such a way that the power to the coil is reduced until atrial pressure returns to the set-point.

The invention has been described in an illustrative manner, and it is to be understood that the terminology which has been used is intended to be in the nature of word of description rather than of limitation.

Obviously, many modifications and variations of the present invention are possible in light of the above teachings. It is, therefore, to be understood that within the scope of the appended claims, the invention may be practiced otherwise than as specifically described.

The embodiments of the invention in which an exclusive property or privilege is claimed are defined as follows:

1. An electromagnetically controlled fluid flow heart valve comprising, housing means defining a passageway having an inlet side and an outlet side, a disk occluder disposed within said passageway having a closed position wherein said disk occluder occludes fluid flow through said passageway and an open position wherein said disk occluder permits fluid flow through said passageway, fulcrum means configured to cause said disk occluder to pivot on an off center pivot axis between said open and closed positions, permanent magnet means carried by said disk occluder having pairs of radially spaced pole faces of opposite magnetic polarity disposed respectively on opposite sides of said pivot axis and an electromagnet carried by said housing means and disposed about said disk occluder, said electromagnet having at least on annular coil that is configured to be energized with direct current, said annular coil when energized producing a first magnetic field, said permanent magnet means causing a second magnetic field to emanate from said pairs of pole faces of said permanent magnet means, said first magnetic field interacting with said second magnetic field to produce magnetic forces on said disk occluder at opposite sides of said pivot axis whereby the interactions of the first and second magnetic fields causes the disc occluder to move to the open or closed position.

2. The valve according to claim 1 wherein said permanent magnet means has first and second portions located respectively on opposite sides of said pivot axis, and wherein said electromagnet is disposed adjacent said passageway and has a magnetic circuit including first, second and third magnetic poles that are axially spaced from each other in a longitudinal direction of said passageway, said second pole being located between said first and third poles, said second pole being of magnetic polarity opposite a magnetic polarity of said first and third poles, said first and second portions of said permanent magnet means being disposed opposite said second pole when said disk occluder is in said closed position, said first and second portions of said permanent magnet means having respective magnetic poles of the same magnetic polarity that respectively face said magnetic poles of said magnetic circuit.

3. The valve according to claim 1 wherein said permanent magnet means is a permanent magnet of annular configuration and wherein said electromagnet has an annular E-shaped magnetic core.

4. The valve according to claim 1 where said permanent magnet means has first and second portions that are located respectively on opposite sided of said pivot axis, and wherein said electromagnet has magnetic circuit having a higher permeability in the vicinity of the permanent magnet means on one side of said pivot axis and having a lower permeability in the vicinity of said permanent magnet means on one opposite side of said pivot axis.

5. The valve according to claim 1 where the disk occluder has a first larger area portion located on a first side of said pivot axis and a second smaller area portion located on a second opposite side of said pivot axis, said first larger area portion having an outer peripheral edge, and wherein said electromagnet includes a magnetic circuit that comprises a pair of spaced annular poles of ferromagnetic material that extend coextensive with said outer peripheral edge of said first larger area portion of said disk occluder that is located on said first side of said pivot axis, said annular poles terminating at said pivot axis whereby the magnetic force exerted by said electromagnet on said disk occluder is greater on said larger area portion than on said smaller area portion.

6. The valve according to claim 1 wherein said electromagnet has a magnetic circuit comprised of a C-shaped toroidal segment of ferromagnetic material and wherein said coil is of annular shape and with a section thereof disposed within said toroidal segment, said toroidal segment being substantially coextensive with a portion of said disk occluder.

7. An electromagnetically controlled heart valve apparatus comprising housing means, said housing means having walls defining a passageway having an inlet side and an outlet side, a disk occluder disposed within said passageway having a close position wherein said disk occludes fluid flow through said passageway and an open position wherein said disk occluder permits fluid flow through said passageway, fulcrum means configured to cause said disk occluder to pivot on an off center pivot axis between said open an closed positions, said disk occluder having a first portion located at a first side of said pivot axis and having a second portion located at a second side of said pivot axis that is opposite said first side, first and second permanent magnets carried by aid disk occluder disposed respectively on opposite sides of said pivot axis, and an electromagnet having a coil and a magnetic circuit, said coil disposed adjacent said walls of said housing means that defines said passageway, said magnetic circuit including a pair of spaced poles located adjacent said wills of said housing means that defines said passageway, each said permanent magnet having a first pole face that faces said pivot axis and a second pole face that faces said spaced poles, said spaced poles having magnetic polarities the magnetic polarities of said first pole faces of said permanent magnets being different and the magnetic polarities of said second pole faces of said permanent magnets being different, said coil when energized producing a magnetic flux at said spaced poles of a predetermined magnetic polarity, the magnetic polarity of said spaced poles and permanent magnets being such that magnetic forces are developed that tend to force one side of said disk occluder located at one side of fulcrum means in a first direction and to force a opposite side of said disk occluder located on an opposite side of said fulcrum means in an opposite direction.

8. The valve apparatus according to claim 7 where said disk occluder has an outer peripheral edge and wherein each of said permanent magnets is of arcuate configuration and is disposed adjacent said outer peripheral edge of said disk occluder, and each of said poles is an annulus of ferromagnetic material surrounding the outer peripheral edge of said disk occluder when it is in the closed position and said poles being spaced axially from each other in a longitudinal direction of said passageway.

* * * * *